United States Patent
Rajasekharan et al.

(10) Patent No.: US 10,302,552 B2
(45) Date of Patent: May 28, 2019

(54) APPARATUS, COMPOSITION AND METHOD FOR DETERMINATION OF CHEMICAL OXIDATION DEMAND

(71) Applicant: Hach Company, Loveland, CO (US)

(72) Inventors: Vishnu V. Rajasekharan, Fort Collins, CO (US); John Lee, Fort Collins, CO (US); Richard E. Leggett, Dickinson, TX (US)

(73) Assignee: HACH COMPANY, Loveland, CO (US)

( * ) Notice: Subject to any disclaimer, the term of this patent is extended or adjusted under 35 U.S.C. 154(b) by 128 days.

(21) Appl. No.: 14/521,713

(22) Filed: Oct. 23, 2014

(65) Prior Publication Data

US 2015/0108009 A1    Apr. 23, 2015

Related U.S. Application Data

(60) Provisional application No. 61/894,906, filed on Oct. 23, 2013.

(51) Int. Cl.
| | |
|---|---|
| *G01N 21/05* | (2006.01) |
| *G01N 33/18* | (2006.01) |
| *G01N 21/27* | (2006.01) |
| *G01N 21/31* | (2006.01) |

(52) U.S. Cl.
CPC .......... *G01N 21/05* (2013.01); *G01N 21/272* (2013.01); *G01N 21/31* (2013.01); *G01N 33/1806* (2013.01); *G01N 2021/317* (2013.01)

(58) Field of Classification Search
CPC ........ G01N 21/01; G01N 21/03; G01N 21/05; G01N 21/17; G01N 21/25; G01N 21/27; G01N 21/272; G01N 21/31; G01N 33/00; G01N 33/18; G01N 33/1806; C25B 1/00–34; C25B 9/00–20
USPC ....................................................... 205/335
See application file for complete search history.

(56) References Cited

U.S. PATENT DOCUMENTS

| | | | |
|---|---|---|---|
| 2,758,090 | A | 8/1956 | Mills et al. |
| 4,783,394 | A | 11/1988 | Hirose et al. |
| 6,183,695 | B1 | 2/2001 | Godec et al. |
| 6,623,974 | B1 | 9/2003 | Horan et al. |
| 8,449,756 | B2 | 5/2013 | Monzyk et al. |
| 2001/0051378 | A1 | 12/2001 | Radmacher et al. |
| 2006/0205083 | A1* | 9/2006 | Zhao ................. G01N 27/305 436/62 |
| 2007/0189923 | A1 | 8/2007 | Lenhard et al. |

(Continued)

FOREIGN PATENT DOCUMENTS

| | | |
|---|---|---|
| CN | 102912366 A | 2/2013 |
| DE | 68903367 T2 | 5/1993 |
| DE | 60131747 T2 | 11/2008 |

(Continued)

OTHER PUBLICATIONS

Zhang et al (Chinese Chemical Letters, 21, 2010, 951-954).*

(Continued)

*Primary Examiner* — Alexander W Keeling

(57) ABSTRACT

Methods for measuring chemical oxygen demand, a composition and a kit useful for measuring chemical oxygen demand, a method for calibrating a chemical oxygen demand analysis method, and a method for determining carbonaceous chemical oxygen demand are disclosed.

8 Claims, 12 Drawing Sheets

(56) References Cited

U.S. PATENT DOCUMENTS

| | | | | |
|---|---|---|---|---|
| 2009/0205973 | A1* | 8/2009 | Monzyk | C25B 1/00 |
| | | | | 205/548 |
| 2014/0346052 | A1* | 11/2014 | Ozaki | G01N 21/65 |
| | | | | 205/335 |

FOREIGN PATENT DOCUMENTS

| | | | |
|---|---|---|---|
| EP | 0082590 B1 | 9/1985 | |
| EP | 0471784 B1 | 7/1996 | |
| WO | 2002/006160 A2 | 1/2002 | |
| WO | WO 02099410 A1 * | 12/2002 | G01N 27/404 |

OTHER PUBLICATIONS

Tian et al (Journal of Environmental Sciences, 20, 2008, 252-256).*
Jiang et al (Separation and Purification Technology, 68, 2009, 227-231).*
Boyle (Technical Information Series, 9, 1997, 1-24).*
Hur et al (Sensors, 10, 2010, 2460-2471).*
Bouzek et al (Electrochemistry Communications, 1, 1999, 370-374).*
Perez-Sicairos et al (Wastewater treatment via electrochemically generated ferrate and commercial ferrate, Desalination and Water Treatment, vol. 52, issue 37-39, pp. 6904-6913, published online Aug. 8, 2013, referred to as Perez herein).*
Korenaga et al (Continuous-flow injection analysis of aqueous environmental samples for chemical oxygen demand, Analyst, 106, pp. 653-662, 1981).*
Jirka et al ("Micro Semi-Automated Analysis of Surface and Wastewaters for Chemical Oxygen Demand", Analytical Chemistry, vol. 47, No. 8, 1975, pp. 1397-1402) (Year: 1975).*
Cuesta et al ("Rapid determination of chemical oxygen demand by a semi-automated method based on microwave sample digestion, chromium(VO) organic solvent extraction and flame atomic absorption spectrometery", Analytical Chimica Act, 372, 1998, pp. 399-409) (Year: 1998).*
Vernier ("Colorimeter") (Year: 2012).*
Karlis Svanks, "Oxidation of Ammonia in Water by Ferrates (VI) and (IV)," Water Resources Center, Engineering Experiment Station, The Ohio State University, 1976.
Wayne Boyles, "The Science of Chemical Oxygen Demand," Technical Information Series, Booklet No. 9, 1997, pp. 1-24.
Rohan Gandhi, "Treatment of Combined Sewer Overflows Using Ferrate (VI)," The School of Graduate and Postdoctoral Studies, The University of Western Ontario, 2013.
J.-Q. Jiang et al., "Progress in the development and use of ferrate(VI) salt as an oxidant and coagulant for water and wastewater treatment", Water Research, 2002, vol. 36, pp. 1397-1408.
Claude A. O. Rosell "The Ferrates," J. Am. Chem. Soc, 1895, vol. 17, No. 10, pp. 760-769.
Ferrate—Layman's Explanation, available at http://www.ferrate.eu/pdf/laymanexplanation.pdf, accessed Jul. 7, 2015.
D. Tiwari et al., "Ferrate(VI) in the Treatment of Wastewaters: A New Generation Green Chemical," Waste Water—Treatment and Reutilization, 2011, pp. 241-276.
http://www.youtube.com/watch?v=2L906yG0-14, Versuche mit Ferrat(VI) (Experiments with ferrate(VI)), published on Jun. 6, 2013, accessed: Dec. 23, 2014.
James D. Carr, "Use of Potassium Ferrate in Oxygen Demand Measurement," Report No. EPA-600/7-77-099, 1977.
R. K. Sharma, "Textbook of Coordination Chemistry", Discovery Publishing House, 2007, pp. 124-125.
Gary Wulfsberg, "Principles of Descriptive Inorganic Chemistry", University Science Books, 1991, pp. 142-143.
A. F. Holleman et al., "Inorganic Chemistry", Academic Press, 1995, pp. 1457-1458.
Gary M. Brittenham, "The Development of Iron Chelators for Clinical Use", CRC Press, 1994, pp. 37-38.
K. M. Mackay et al., "Introduction to Modern Inorganic Chemistry", 6th edition, 2002, pp. 334-335.
Amit Arora "Text Book of Inorganic Chemistry", Discovery Publishing House, 2005, pp. 691-692.
http://www.wou.edu/las/physci/ch412/pourbaix.htm, last modified: Nov. 6, 2012; accessed: Dec. 23, 2014.
http://en.wikipedia.org/wiki/Chromium, last modified: Dec. 13, 2014 accessed: Dec. 23, 2014.
Virender K. Sharma, "Potassium ferrate(VI): an environmentally friendly oxidant," Advances in Environmental Research, 2002, vol. 6, pp. 143-156.
G. Hill et al., "Chemistry in Context", 5th edition, 2000, p. 202.
S. B. Quek et al., "Bio-Electrochemical Sensor for Fast Analysis of Assimilable Organic Carbon in Seawater," Journal of Biosensors & Bioelectronics, 2014, vol. 5, No. 2, pp. 1-4.
L. Li et al., "Determination of chemical oxygen demand of nitrogenous organic compounds in wastewater using synergetic photoelectrocatalytic oxidation effect at TiO2 nanostructured electrode," Analytica Chimica Acta 754, 2012, pp. 47-53.
G. W. Thompson et al., "Preparation and Purification of Potassium Ferrate. VI," J. Am. Chem. Soc., 1951, vol. 73, No. 3, pp. 1379-1381.
D. Y. Stupin et al., "Features of Chemiluminescence Arising in Oxidation of Luminol with Ferrate(VI) Ions in Alkaline Solutions", Russian Journal of General Chemistry, 2001, vol. 71, No. 5, pp. 659-663.
I. Ciabatti et al. "Treatment and reuse of dyeing effluents by potassium ferrate", Desalination, 2010, vol. 250, pp. 222-228.
V. Shastry et al. "Waste Water Treatment Using Eco Friendly Oxidising Agent Fe (VI)", Hydrology Current Research, 2011, vol. 2, No. 5, pp. 1-4.
N. Graham et al. "The influence of pH on the degradation of phenol and chlorophenols by potassium ferrate", Chemosphere, 2004, vol. 56, pp. 949-956.
B. Yang et al. "Removal of selected endocrine disrupting chemicals (EDCs) and pharmaceuticals and personal care products (PPCPs) during ferrate(VI) treatment of secondary wastewater effluents", Water Research, 2012, vol. 46, pp. 2194-2204.
V. K. Sharma et al. "Ferrate(VI) Enhanced Photocatalytic Oxidation of Pollutants in Aqueous TiO2 Suspensions", Envioron. Sci. Pollut. Res., 2008, vol. 15, No. 1, pp. 1-11.
Y. Lee et al., "Ferrate (Fe(VI)) Application for Municipal Wastewater Treatment: A Novel Process for Simultaneous Micropollutant Oxidation and Phosphate Removal", Environ. Sci. Technol., 2009, vol. 43, pp. 3831-3838.
V K. Sharma et al., "Ferrates (iron(VI) and iron(V)): Environmentally friendly oxidants and disinfectants", Journal of Water and Health, 2005, pp. 1-15.
P. J. Dorathi et al. "Sonochemical degradation of p-chlorophenol in aqueous solution using hypervalent iron", Indian Journal of Chemical Technology, 2010, vol. 17, pp. 111-119.
C. Li et al., "A study of the preparation and reactivity of potassium ferrate", Chemosphere, 2005, vol. 61, pp. 537-543.
E. S. Batarseh et al., "Liquid Sodium Ferrate and Fenton's Reagent for Treatment of Mature Landfill Leachate", Journal of Environmental Engineering, 2007, pp. 1042-1050.
H. J. Zhang et al. "Electrogeneration of ferrate (VI) in low concentration NaOH solution for flow-injection-chemiluminescence detection", Chinese Chemical Letters, 2010, vol. 21, pp. 951-954.
T. Berner et al., "Toxicological Review of Hexavalent Chromium," EPA, 2010.
Edward Todd Urbansky, "Total organic carbon analyzers as tools for measuring carbonaceous matter in natural waters", Journal of Environmental Monitoring, 2001, vol. 3, No. 1, pp. 102-112.
V. K. Sharma et al., "Oxidation of Ammonia by Ferrate(VI)", Journal of Environmental Science and Health, 1998, vol. A33, No. 4, pp. 635-650.
J.-Q. Jiang et al., "The online generation and application of ferrate(VI) for sewage treatment—A pilot scale trial", Separation and Purification Technology, 2009, vol. 68, No. 2, pp. 227-231.
International Search Report corresponding to Application No. PCT/US2014/061952, dated Jan. 20, 2015.

(56) References Cited

OTHER PUBLICATIONS

International Search Report corresponding to Application No. PCT/US2014/061971, dated Jan. 26, 2015.
International Search Report corresponding to Application No. PCT/US2014/061958, dated Mar. 25, 2015.

* cited by examiner

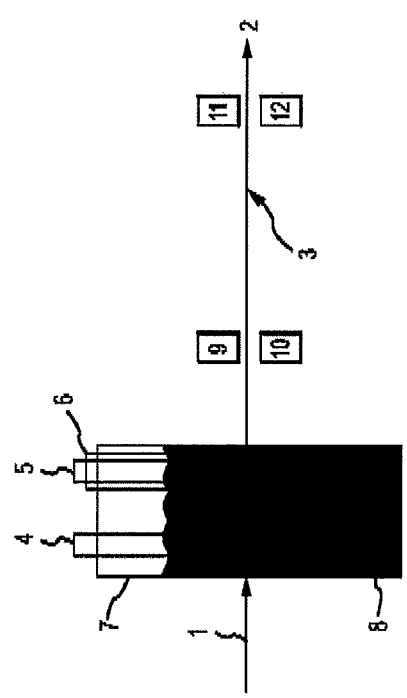
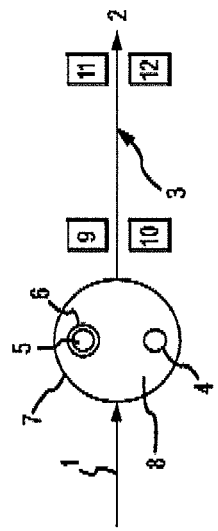
FIG.2A
FIG.2B

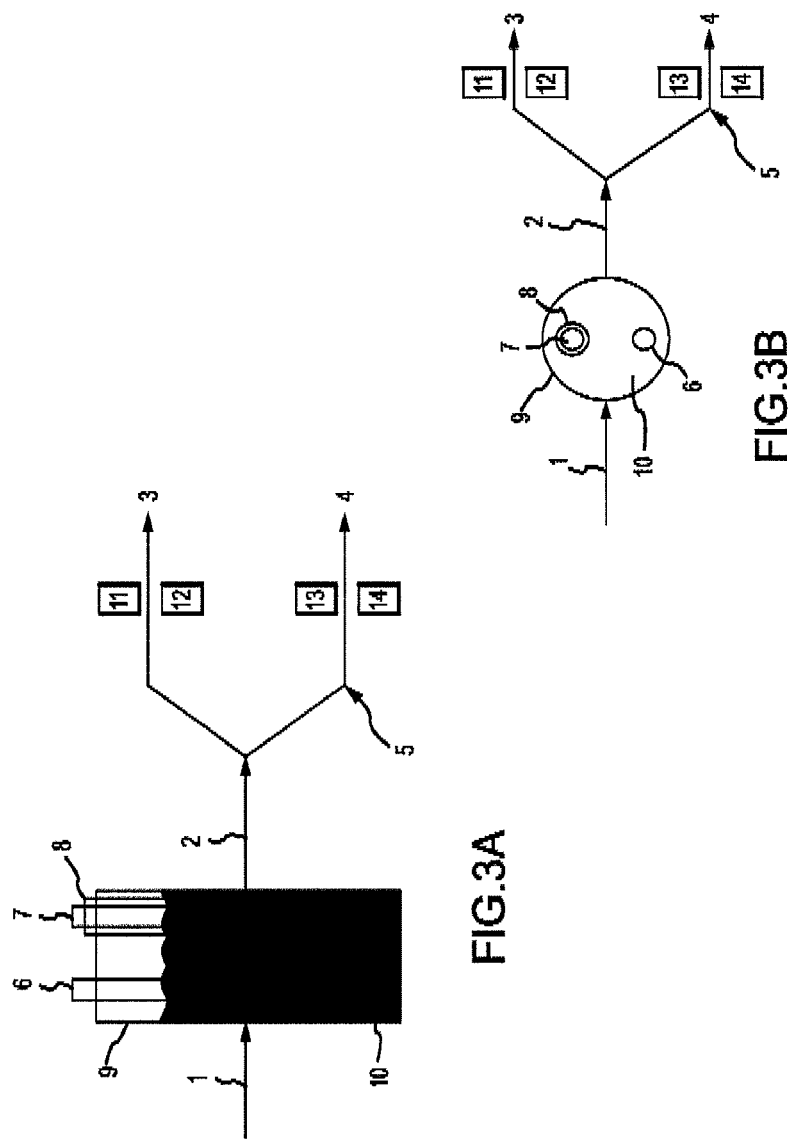

APPARATUS, COMPOSITION AND METHOD FOR DETERMINATION OF CHEMICAL OXIDATION DEMAND

CROSS-REFERENCE TO RELATED APPLICATIONS

This application claims priority to U.S. provisional application No. 61/894,906 filed Oct. 23, 2013.

INTRODUCTION

This application relates generally to the analysis of Chemical Oxygen Demand ("COD") in water and, more particularly, to the analysis of COD using a non-toxic chemical oxidant. Oxygen demand is an important parameter for determining the amount of organic pollution in water. The test has its widest application in measuring waste loadings of treatment plants and in evaluating the efficiency of treatment processes. Other applications include testing lake and stream water samples for organic pollution. Oxygen demand testing does not determine the concentration of a specific substance; rather, it measures the effect of a combination of substances and conditions. Because oxygen demand is not a pollutant, it poses no direct threat to fish or other life. It can, however, pose an indirect threat to living organisms by reducing the level of dissolved oxygen. There are three widely-used methods of measuring oxygen demand. Two measure oxygen demand directly: Biochemical Oxygen Demand (BOD) and Chemical Oxygen Demand (COD). A third method-Total Organic Carbon (TOC)-measures oxygen demand indirectly using correlation.

COD tests use a strong chemical oxidant in an acid solution and heat to oxidize organic material to $CO_2$ and $H_2O$ and other oxidation products. By definition, chemical oxygen demand is a measure of the oxygen equivalent of the organic matter content of a sample that is susceptible to oxidation by a strong chemical oxidant. Oxygen demand is determined by measuring the amount of oxidant consumed using titrimetric or photometric methods. The test is not adversely affected by toxic substances, and test data is available in 1-½ to 3 hours, providing fast water quality assessment and process control.

Chemical species presently used to assess COD include $K_2Cr_2O_7$ ("dichromate method"), $Mn_2(SO_4)_3$ ("Manganese III method"), $KMnO_4$, $Ce(SO_4)_2$, $K_2S_2O_8$ and $O_3$ (Ozone). Using the dichromate method there are two digestion methods used in the COD test: the older Macro Digestion Method, and the Micro Digestion Method. The Macro Digestion Method requires a considerable amount of space, equipment and volume of reagents for each test. Each set-up includes a flask, a glass condenser with hose, a hot plate, a laboratory stand, and clamps. Sample volumes are also relatively large. Because of these inconveniences, the macro method has been virtually replaced by the micro method. The Micro Digestion Method minimizes reagent consumption and reduces the required space and equipment to one reactor block that will digest up to 25 samples at one time. Each test set-up is a self-contained disposable vial, which is inserted into a block heater. Reagent and sample volumes are considerably smaller, which decreases reagent cost and waste volume. The two-hour digestion time can be reduced if caution is observed. Many types of waste are digested completely in 30 minutes or less at 150° C., the normal operating temperature. The time of complete digestion can be recognized through experience, or by using a colorimetric reading with the micro method discussed later. In this approach, many consecutive readings are taken on a single sample, allowing a final determination of when the reaction is complete.

After the oxidation step is completed, the amount of dichromate consumed is determined titrimetrically or colorimetrically. Either the amount of reduced chromium (trivalent) or the amount of unreacted dichromate (hexavalent) can be measured. End products of the reaction are carbon dioxide, water, and various states of the chromium ion. Colorimetric procedures are easier and quicker to run and are generally more accurate. However, when samples are turbid or colored, or if a spectrophotometer is not available, a titrimetric procedure should be used. Titrimetric procedures require a higher degree of operator skill and take longer to perform. The lowest range and highest sensitivity colorimetric COD test available has a detection range from 0.7-60 mg/L COD, where measurements are made at a wavelength of 350 nm. The maximum sensitivity is at 345 nm, but the test measurement is made at 350 nm for instrumentation considerations. The calibration line for this test has a negative slope. The amount of hexavalent chromium remaining after digestion is measured and it decreases as the COD concentration increases.

Hexavalent chromium ("Cr(VI)" or "chromium-6") is a known carcinogen and mutagen and so exposure and disposal are of great concern. Health effects related to exposure to ingested chromium-6 are presently the subject of active investigation by the EPA and other government agencies as well as private researchers. In its draft "Toxicological Review of Hexavalent Chromium" released in September 2010 for public comment, the EPA states that there is "evidence of an association between oral exposure to hexavalent chromium and stomach cancer in humans." Further, the report notes that "available evidence indicates that chromium interacts with DNA, resulting in DNA damage and mutagenesis."

Apparatus, Composition and Method for Determination of Chemical Oxidation Demand In one embodiment, a method for measuring chemical oxygen demand in a flow-through EC cell having an integrated spectrophotometer, comprises: providing a flow-through EC cell adapted to electrolyze liquid cell contents having an iron anode, a cathode and a light-transparent sample cell; providing an amount of alkaline hydroxide to the liquid cell contents; applying a current density to the liquid cell contents at an electrical potential sufficient to oxidize a portion of the iron anode to a higher valence comprising Fe(VI); providing a light source for projecting light through the sample cell; providing a detector for detecting the light after passing through the sample cell; optimizing pH of the liquid cell contents to between about 3 and about 11 such that oxidizable organic species are detectable; measuring the baseline light absorbance at a wavelength diagnostic of ferrate ion; introducing a sample into the EC cell in proximity to the anode; and measuring the light absorbance of the sample at a wavelength diagnostic of depletion of ferrate ion and comparing the light absorbances, thereby determining the oxygen demand of the sample.

In another embodiment, a method for measuring chemical oxygen demand in a flow-through EC cell having a separate spectrophotometer, comprises: providing a flow-through EC cell adapted to electrolyze liquid cell contents having an iron anode and a cathode; providing a light-transparent sample cell in liquid communication with the EC cell; providing a light-transparent blank cell in liquid communication with the EC cell; providing an amount of alkaline hydroxide to the liquid cell contents; applying a current density to the EC cell at an electrical potential sufficient to oxidize a portion of the iron anode to create a solution comprising Fe(VI); providing one or more light sources for projecting light through either or both blank and sample cells; providing one or more detectors for detecting the light passing through either or both blank and sample cells; optimizing pH of the Fe(VI) solution prior to introduction of the liquid cell contents into the sample cell to between about 3 and about 11 such that oxidizable organic species are detectable; combining the sample and the Fe(VI) solution in the sample cell; and measuring and comparing the light absorbance in both blank and the sample cells at a wavelength diagnostic of depletion of ferrate ion, thereby determining the oxygen demand of the sample.

In a further embodiment, a method for measuring chemical oxygen demand (COD) using at least one higher valence iron species, comprises: providing a known amount of higher valence Fe in a COD analyzer; optimizing the pH in the COD analyzer to be between about 3 and about 11 such that oxidizable organic species are detectable; combining said known amount of higher valence Fe with a water sample suspected of containing materials having oxygen demand in the COD analyzer; measuring a parameter indicative of the at least one higher valence Fe species concentration in the water sample caused by the materials having oxygen demand; combining said known amount of higher valence Fe with a blank water sample in the COD analyzer; measuring a parameter indicative of the at least one higher valence Fe species concentration in the blank water sample; and calculating the difference in measurements between the water sample and the blank water sample caused by said materials having oxygen demand, whereby the oxygen demand is quantified.

In yet another embodiment, a method for measuring chemical oxygen demand (COD) in a laboratory environment using at least one higher valence iron species, comprises: providing a known amount of Fe(VI) into a first container; introducing a water sample suspected of containing materials having oxygen demand into the first container; optimizing the pH in the first container to be between about 3 and about 11 such that oxidizable organic species are detectable; providing a known amount of Fe(VI) into a second container; introducing a blank water sample into the second container; adjusting the pH in the second container to be substantially the same as in the first container; measuring a parameter indicative of the difference in concentration of the higher valence iron species between the water sample and the blank water sample caused by the materials having oxygen demand whereby the oxygen demand is quantified.

The following are additional embodiments:

A method, wherein the cathode comprises iron.

A method, wherein the alkaline hydroxide is chosen from alkali metal hydroxides.

A method, wherein the temperature of the EC cell is maintained between about 35 C and about 75 C.

A method, wherein the current density ranges from about 0.001 A/cm$^2$ to about 10 A/cm$^2$.

A method, additionally comprising the step of: monitoring voltage in the EC cell as the liquid cell contents are introduced as an indication of oxygen demand.

A method, wherein the Fe(VI) is present in the anion $[FeO_4]^{2-}$.

A method, wherein optimizing pH comprises the additional steps of: changing the pH of an aliquot of a first sample to a first pH and measuring its absorbance; changing the pH of a second aliquot of the same sample to a second pH and measuring its absorbance; determining the difference between the first and second absorbance measurements, whereby the difference indicates the oxidation rate of the organic compounds at the selected pHs; and repeating the first three steps to find the maximum difference thereby identifying the optimal pH for the sample.

A method, wherein the gas-generating portion of said cathode is segregated from solution by a hydrogen-specific membrane or standard frit that allows current through but substantially segregates the hydrogen from the ferrate-containing solution.

A method, wherein the blank and sample cells are arranged in series.

A method, wherein the blank and sample cells are arranged in parallel.

A method, wherein the measurement parameter is optical absorbance at a wavelength diagnostic of Fe(VI).

A method, wherein the wavelength is from about 500 to about 515 nm.

A method, wherein the measurement parameter is electrochemical signal.

A method, wherein the measurement parameter is turbidity.

A method, wherein the measurement parameter is magnetic.

A method, wherein the measurement parameter is gravimetry.

A method, wherein the COD analyzer comprises an electrochemical cell.

A method, wherein the parameter is optical absorbance and measurement of the water and blank samples requires providing a spectrophotometer to measure and determine optical absorbance at a wavelength diagnostic of Fe(VI) absorbance.

A method, wherein the containers are optically transparent.

A method, wherein Fe(VI) is present in a compound chosen from $Na_2FeO_4$ and $K_2FeO_4$.

A method, wherein the parameter is electrochemical.

A method, wherein the electrochemical measurement parameter is redox potential.

Also disclosed herein is a composition of matter, comprising: a higher valence iron species in a concentration sufficient to oxidize any suspected oxidizable organic constituents in a sample; a buffer capable of buffering a sample to a desired pH range; and a ligand for solubilizing insoluble forms of Fe.

A composition, wherein the higher valence iron species is derived from a ferrate salt chosen from water-soluble salts.

A composition, wherein said ferrate salt is selected from alkali metal salts.

A composition, wherein the ferrate salt is chosen from $K_2FeO_4$ and $Na_2FeO_4$.

A composition, wherein the buffer has little or no chemical oxygen demand.

A composition, wherein the buffer is chosen from phosphate, acetate, and borate.

A composition, wherein the ligand has little or no chemical oxygen demand.

A composition, wherein the ligand is chosen from EDTA, mono-and di-basic phosphate and DMG.

A composition, wherein an amount of Fe(II) and/or Fe(III) is present.

A composition, wherein an amount of base is present at a concentration of from about 1M to about 16 M. The base may be NaOH or KOH.

Further disclosed herein is a kit, comprising: a container having the composition of matter disclosed herein and a separate container having a different compatible oxidant.

In yet another embodiment, a method for calibrating a COD analysis method, comprises: providing a known amount of higher valence iron species in a COD analyzer; optimizing the pH in the COD analyzer such that a calibrant is substantially completely oxidized; combining the known amount of higher valence iron species with a water sample containing a known amount of the calibrant in the COD analyzer; measuring a parameter indicative of the at least one higher valence Fe species concentration in the water sample caused by the calibrant; repeating the third and fourth steps with different known amounts of the calibrant to create a measurement range; measuring a parameter indicative of the at least one higher valence Fe species concentration in a blank water sample; and creating a calibration curve using the measurement parameters for each known amount of the calibrant and the blank value.

A method, wherein the calibrant is selected from the group consisting of potassium hydrogen phthalate (KHP), glucose, glutamic acid, benzoquinone, and combinations thereof.

A method, wherein the calibrant is KHP and the pH is optimized to be between about 3 and about 11.

Further disclosed herein is a method for determining carbonaceous chemical oxygen demand in a sample, comprising: preventing nitrogen-containing compounds from contributing to oxidation in the sample by ferrate ion; after the preventing operation, adding ferrate ion to the sample; measuring a parameter indicative of the amount of ferrate ion in the sample; and determining a carbonaceous chemical oxygen demand value of the sample based on the measured parameter.

A method, wherein the preventing operation comprises adding a nitrogen inhibitor to the sample.

A method, further comprising adding ferrate ion to a blank sample; and measuring a parameter indicative of the amount of ferrate ion in the blank sample, and wherein the determining operation comprises calculating a difference in the measured parameters between the sample and the blank sample and determining the carbonaceous chemical oxygen demand value of the sample based on the difference.

A method, wherein the measuring operation regarding the sample comprises passing light through the sample and measuring an absorbance of light passed through the sample at a wavelength diagnostic of ferrate ion; and the measuring operation regarding the blank sample comprises passing light through the blank sample and measuring an absorbance of light passed through the blank sample at the wavelength diagnostic of ferrate ion.

BRIEF DESCRIPTION OF THE DRAWINGS

In the drawings:

FIGS. 2A and 2B are schematic representations of an apparatus of another embodiment, FIG. 2A being the side view and FIG. 2B being the top-down view.

FIGS. 3A and 3B are schematic representations of yet another embodiment of the apparatus.

DETAILED DESCRIPTION

Briefly, embodiments disclosed herein include a method and apparatus for COD measurement using higher valence iron compositions. As used herein, the term "higher valence iron species" means those valences of the element iron that are greater than 3, that is, $Fe^{4+}$ (Fe(IV)), $Fe^{5+}$ (Fe(V)) and $Fe^{6+}$ (Fe(VI)). As used herein, the term "ferrate ion" refers to an anion containing iron in a valence state greater than zero, including +1, +2, +3, +4, +5, and +6, unless the context clearly dictates otherwise. One example of a source of ferrate ion is the alkali metal salt $K_2FeO_4$ (potassium ferrate). Iron in the lower valences 0-3 can be oxidized to the higher valences that have sufficient oxidation potential to oxidize organic compounds found in the environment. For example, oxidants such as ozone, hypochlorous acid and hydrogen peroxide, amongst others, are used to oxidize the lower valences of iron to the higher valences.

Figure 6:
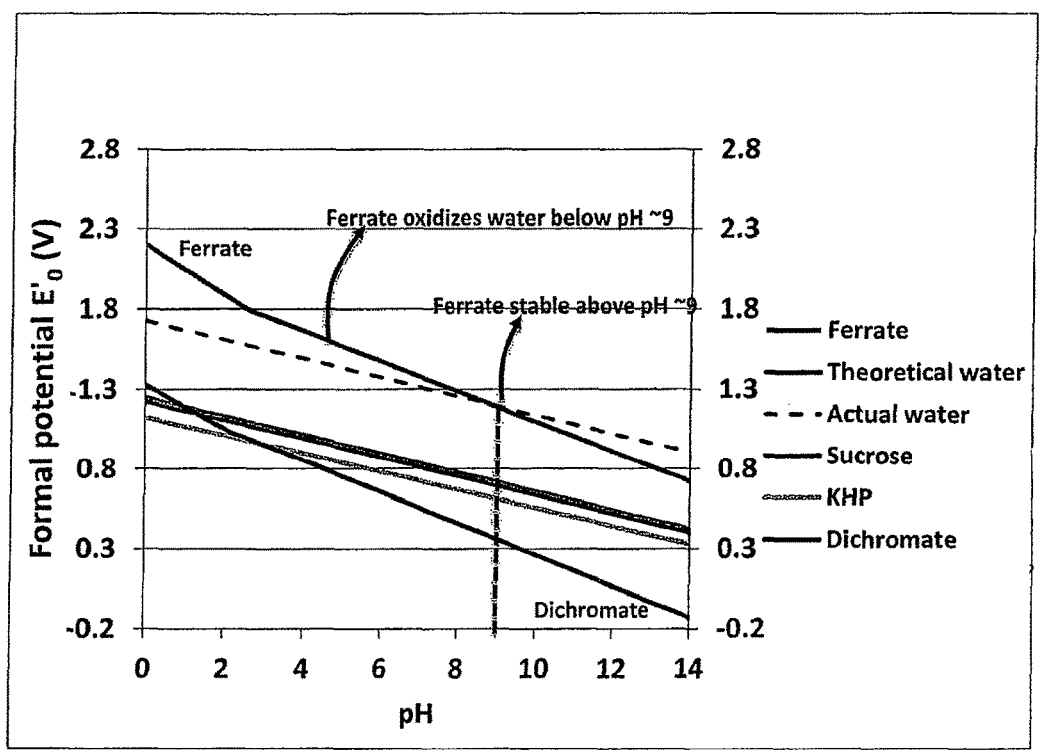
FIG. 6 is a Pourbaix diagram comparing the thermodynamic oxidation efficiency of ferrate and dichromate at about 25 C.
Figure 8A:
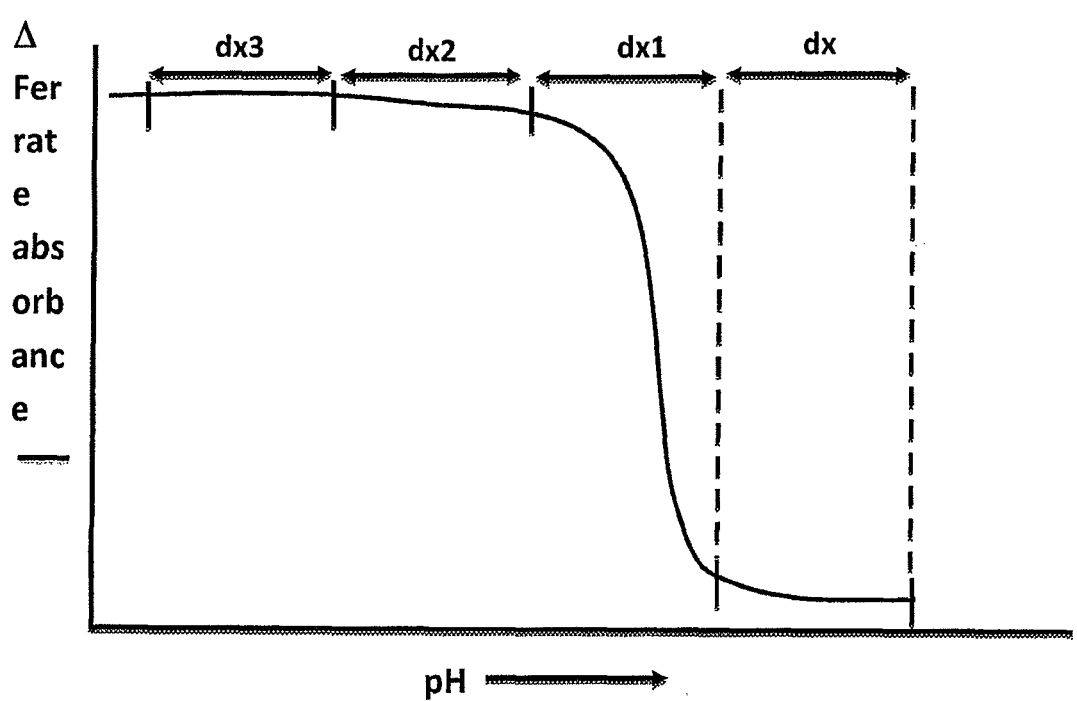
FIGS. 8A and 8B are graphs of ferrate absorbance versus pH, and $E_0$ versus pH, respectively.
Figure 8B:
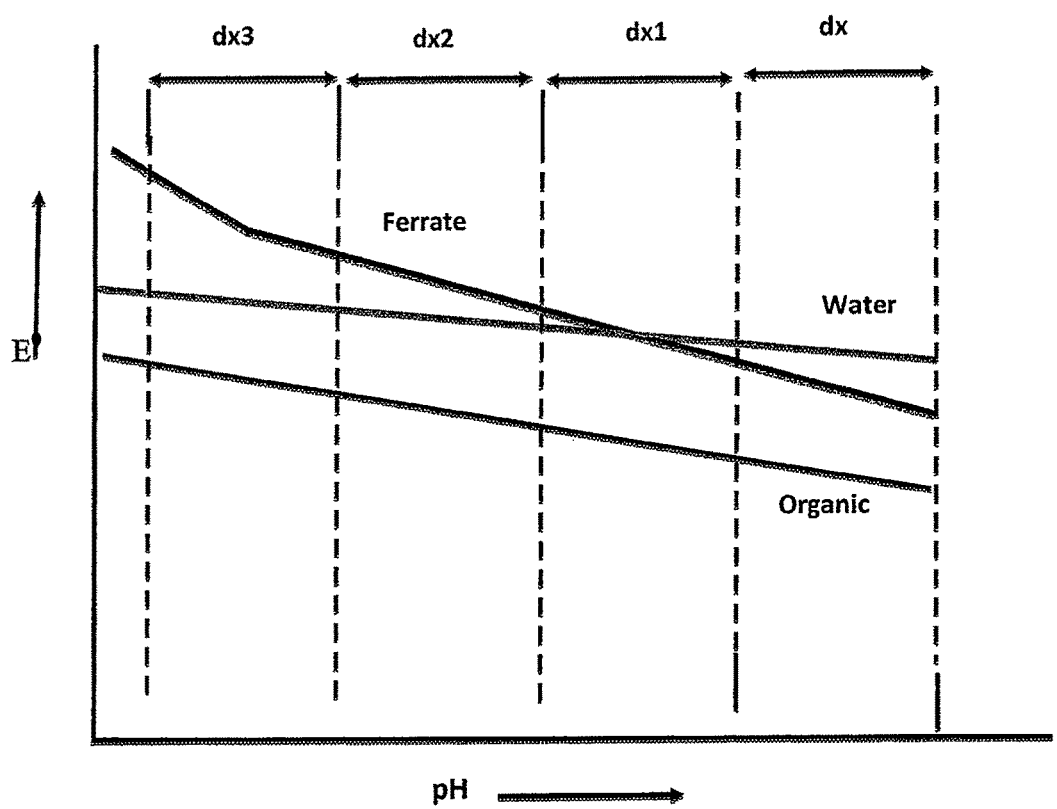

The term "optimizing pH" includes determining the best pH for oxidizing the predominant chemical species present in the sample stream by progressively lowering pH until complete oxidation of the species is achieved. In one embodiment this may involve the additional steps of: a) changing the pH of an aliquot of a first sample to a first pH and measuring its absorbance; b) changing the pH of a second aliquot of the same sample to a second pH and measuring its absorbance; c) determining the difference between the first and second absorbance measurements, whereby the difference indicates the oxidation rate of the organic compounds at the selected pHs; and d) repeating steps a-c to find the maximum difference thereby identifying the optimal pH for the sample. For example in FIG. 8A is shown a schematic for determining the pH range for maximum oxidation efficiency for ferrate-organic systems. Ferrate absorbance at a diagnostic wavelength (504 nm) versus pH is plotted. At acidic pH (regions dx2 and dx3) ferrate oxidation of solely water predominates. As the pH is increased, a transition occurs at dx1 where ferrate oxidation of organics begins. The pH at which this happens can vary from about 6 to about 9, but is typically observed at pH 9, as shown in FIG. 6. The transition can be rapid as shown in the region dx1. At higher pH, typically 9+, ferrate oxidation of organics predominates. Turning to FIG. 8B, ferrate free energy $E_O$ intersects that of water at about pH 9. Below pH 9, (regions dx2-dx3) ferrate oxidation of water begins and becomes more prominent as pH decreases. At pH 9 and above (regions dx-dx1), ferrate preferentially oxidizes organics as opposed to water. Thus, one of ordinary skill may use this guidance as a predictor of where the optimal pH for a particular organic species lies.

The redox potentials for the various organic constituents is readily ascertainable from the CRC, as an example, or by electrochemical measurement. The dependence of the thermodynamic potential of the redox species on the pH of the solution can be determined using the thermochemical constants and Pourbaix's diagram (FIG. 6). A Pourbaix diagram, also known as a potential/pH diagram, $E_H$-pH diagram or a pE/pH diagram, maps out possible stable equilibrium phases of an aqueous electrochemical system. Predominant ion boundaries are represented by lines. The optimal range of the pH for maximizing the oxidation potential for ferrate $[FeO_4]^{2-}$ and dichromate are compared in FIG. 6.

The redox reactions for dichromate and ferrate discussed herein are shown in TABLE 1.

TABLE 1

| Chromium: Redox reactions[2] | | | |
|---|---|---|---|
| In Acid | $Cr_2O_7^{2-} + 14 H^+ + 6e^- \leftrightarrow 2Cr^{3+} + 7H_2O$ | $E_0$ | 1.33 |
| In Base | $CrO_4^{2-} + 4 H_2O + 3e^- \leftrightarrow 2Cr(OH)_3 + 5OH^-$ | $E_0$ | −0.31 |
| Equilibrium reactions and constants | | | |
| | $Cr_2O_7^{2-} + H_2O \leftrightarrow 2HCrO_4^-$ | $pK_{eq}$ | 2.2 |
| | $HCrO_4^- \leftrightarrow CrO_4^{2-} + H^+$ | $pK_{eq}$ | 5.9 |
| Ferrate: Redox reactions[3] | | | |
| In Acid | $FeO_4^{2-} + 8 H^+ + 3e^- \leftrightarrow Fe^{3+} + 4 H_2O$ | $E_0$ | 2.2 |
| In Base | $3FeO_4^{2-} + 8 H_2O + 10e^- \leftrightarrow Fe_3O_4 + 16OH^-$ | $E_0$ | 0.72 |
| Equilibrium reactions and constants | | | |
| | $H_3FeO_4^+ + H^+ \leftrightarrow H_2FeO_4$ | $pK_a$ | 1.6 |
| | $H_2FeO_4 \leftrightarrow HFeO_4^- + H^+$ | $pK_{eq}$ | 3.5 |

[1]http://www.wou.edu/las/physci/ch412/pourbaix.htm
[2]http://en.wikipedia.org/wiki/Chromium
[3]"Potassium Ferrate(VI): An Environmentally Friendly Oxidant" V. K. Sharma, Adv. Environ. Res. 6, 143 (2002).

In one embodiment, a method provides an EC cell for making ferrate in situ and taking measurements during simultaneous ferrate synthesis and ferrate oxidation of organics. The embodiment is directed to a method for measuring chemical oxygen demand in a flow-through EC cell ("EC cell") with an integrated spectrophotometer comprising providing a flow-through EC cell adapted to electrolyze liquid cell contents and having an iron anode, a cathode and a light-transparent sample cell. An amount of alkaline hydroxide is provided to the liquid cell contents so that the resulting pH within the EC cell will be elevated to alkaline conditions. An electrical current is applied to the EC cell contents by conventional means such as powering on a power supply connected to the electrodes and applying a current density to the liquid cell contents at an electric potential sufficient to oxidize a portion of the iron anode to a higher valence comprising Fe(VI). Other valences of iron may also result depending upon the pH of the cell, buffer composition, nature of any ligand, redox potential of the solution, and temperature, such as Fe(II), Fe(III), Fe(IV) and Fe(V). Since the EC cell has a light-transparent portion, colorimetric detection may be effected in the same cell by providing a light source for projecting light through the sample cell, and providing a detector for detecting the light after passing through the sample cell. Since aqueous ferrate is normally dark-blue colored colorimetric detection is well-suited to this method.

The pH of the liquid cell contents is optimized to between about 3 and about 11 such that oxidizable organic species are detectable by the decrease in absorbance that occurs upon oxidation of organics by ferrate, thus reducing the amount of ferrate in solution. The precise pH will depend upon the nature of the organic carbon contents to be oxidized, as is discussed in more detail below. The baseline light absorbance is measured at a wavelength diagnostic of ferrate ion, one candidate wavelength being 504 nm although others within the range of about 500 to about 515 nm may also be operable. This "blank" measurement is done by mixing the same amount of ferrate into the same volume of pure water as the sample water volume, then measuring it to obtain a baseline absorbance. A sample is introduced into the EC cell in proximity to the anode compartment, which is where the iron metal is oxidized to various higher valence iron species such as Fe(IV), Fe(V) and Fe(VI). Without being bound by any particular theory, it is believed that under the conditions of this method the majority of iron is oxidized to $[FeO_4]^{2-}$ (ferrate) ion at a pH greater than 7. Measurement of the light absorbance of the sample at a wavelength diagnostic of depletion of ferrate ion (approximately 500-515 nm), and comparing the light absorbances, permit the determination of the oxygen demand of the sample. The comparison requires subtracting the baseline absorbance measurement from the sample-related absorbance to arrive at the true, or net absorbance due only to the COD of the sample. The net absorbance value can then be correlated with the COD of the sample by reference to a calibration table.

In another embodiment, standard electrochemical cells have a minimum of one cathode and one anode. The anode necessarily is made from iron metal, and the cathode is optionally although preferably also made from iron metal. The $[FeO_4]^{2-}$ ion is generated at the anode. The alkaline hydroxide is chosen from alkali metal hydroxides, including potassium and sodium hydroxide, although others may also be suitable.

In another embodiment of the method the temperature of the EC cell is maintained between about 35 C and about 75 C, with a more preferable temperature range being from about 50 C to about 75 C and a most preferred temperature being about 60 C. EC cell current density is related to the rate of oxidation of iron to ferrate at the anode. The current density may range from about 0.001 A/cm$^2$ to about 10 A/cm$^2$. One of ordinary skill may select a current density that is appropriate for the desired rate of oxidation, taking into consideration issues such as coulombic heating of the solution, hydrogen generation at the cathode, etc.

In another embodiment of the EC cell a membrane or frit separating the anode and cathode is used to segregate hydrogen gas generation from the ferrate ion since Hydrogen permeating the solution may recombine (reduce) the $[FeO_4]^{2-}$ resulting in a lower valence state of the iron, which are undesirable. A suitable separating barrier is a glass frit or a porous polymer membrane having a pore size effective for permitting charge transfer, such as PTFE from Poroex Co., 1/16" coarse pore size, as an example.

Another embodiment of the EC cell monitors the voltage in the EC cell as the liquid cell contents are introduced as an indication of oxygen demand. A voltmeter can be introduced to measure the amount of voltage the cell is being subjected to at the current density employed. The cell voltage is an indication of the potential which provides a means to measure the depletion of ferrate necessary to oxidize any given chemical species present in the cell.

The term ferrate normally refers to iron in a valence state of +6 (Fe(VI)), although it can refer to other valence states of iron including +1, +2, +3, +4, and +5. Ferrate is present in the highly reduced species disodium tetracarbonylferrate $Na_2[Fe(CO)_4]$ and salts of the iron(III) complex tetrachloroferrate $[FeCl_4]^-$. Ferrate(V) $[FeO_4]^{3-}$ and ferrate(IV) $[FeO_4]^{4-}$ oxyanions of iron also exist. (Graham Hill; John Holman (2000) *Chemistry in Context* (5th ed.), Nelson Thornes p. 202).

Ferrate(VI) salts may be generated by oxidizing iron in an aqueous medium with strong oxidizing agents under alkaline conditions, or in the solid state by heating a mixture of iron filings and powdered potassium nitrate (R. K. Sharma (2007), *Text Book Of Coordination Chemistry*, Discovery Publishing House, pp. 124-125). For example, ferrates are produced by heating iron(III) hydroxide with sodium hypochlorite in alkaline solution:

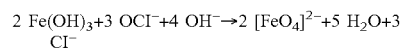
$$2\ Fe(OH)_3 + 3\ OCl^- + 4\ OH^- \rightarrow 2\ [FeO_4]^{2-} + 5\ H_2O + 3\ Cl^-$$

(Gary Wulfsberg (1991), *Principles of descriptive inorganic chemistry*, University Science Books, pp. 142-143). The anion is typically precipitated as the barium(II) salt, forming barium ferrate. Id. Ferrates can also be produced according to recently issued U.S. Pat. No. 8,449,756B2 "Method for Producing Ferrate (V) and/or (VI)" wherein ferrate is made in an electrochemical cell by applying a continuously and automatically varied variable direct current voltage between the anode and the cathode to form the ferrate(V) and/or ferrate(VI), the variable direct current voltage varying between a maximum voltage (Vmax) and a minimum voltage, the minimum voltage (Vmin) is greater than 0 and is a voltage to ensure that formation of an oxide film on a surface of the anode is depressed so that passivation of the anode is largely avoided.

The Fe(VI) anion is unstable at neutral or acidic pH values, decomposing to iron(III):

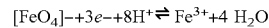
$$[FeO_4]^- + 3e^- + 8H^+ \rightleftharpoons Fe^{3+} + 4\ H_2O$$

The reduction goes through intermediate species in which iron has oxidation states +5 and +4 (Egon Wiberg; Nils Wiberg; Arnold Frederick Holleman (2001), *Inorganic chemistry*, Academic Press, pp. 1457-1458). These anions are more reactive than Fe(VI) (Gary M. Brittenham (1994), Raymond J. Bergeron, ed., *The Development of Iron Chelators for Clinical Use*, CRC Press, pp. 37-38). In alkaline conditions ferrates are more stable, lasting for about 5 to 50 hours at pH 9 or above. Id.

Aqueous solutions of ferrates are pink when dilute, and deep red or purple at higher concentrations. The ferrate ion is a stronger oxidizing agent than permanganate (Kenneth Malcolm Mackay; Rosemary Ann Mackay; W. Henderson (2002), *Introduction to modern inorganic chemistry* (6th ed.), CRC Press, pp. 334-335), and will oxidize chromium (III) to dichromate, (Amit Arora (2005), *Text Book Of Inorganic Chemistry*, Discovery Publishing House, pp. 691-692) and ammonia to molecular nitrogen (Karlis Svanks (June 1976), "Oxidation of Ammonia in Water by Ferrates (VI) and (IV)" (PDF), Water Resources Center, Ohio State University, p. 3, retrieved Sep. 30, 2013).

Figure 1:
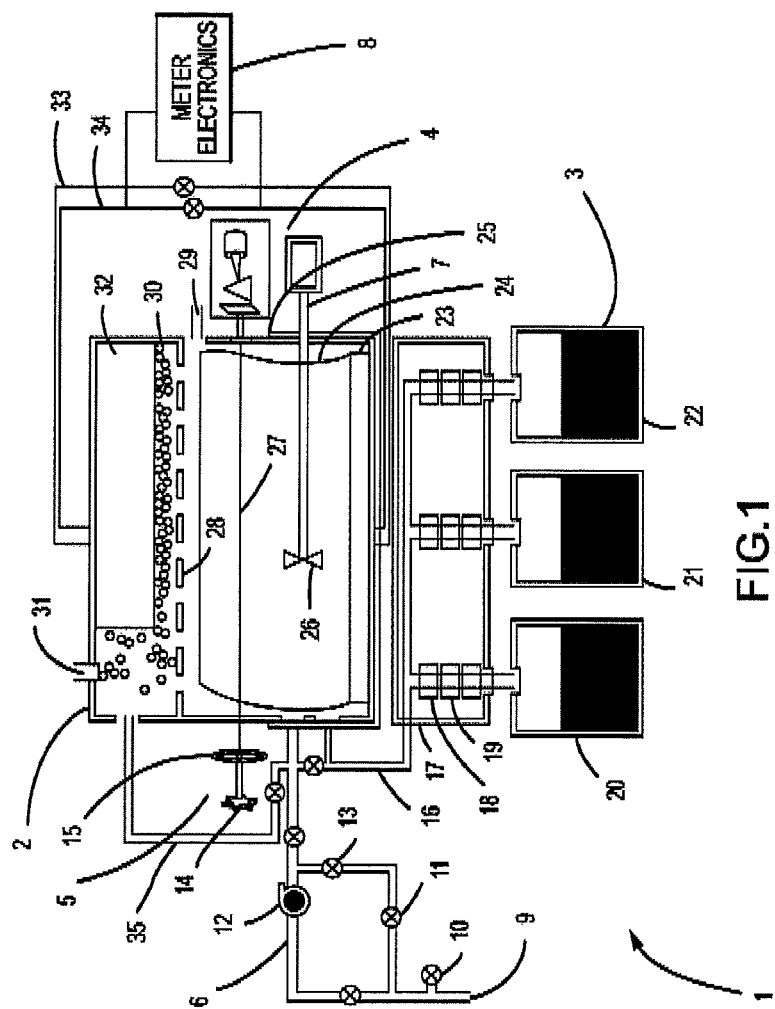
FIG. 1 is a schematic representation of an embodiment of the apparatus for measuring COD using a higher valence iron species, such as ferrate to oxidize organic species.

Reference will now be made in detail to exemplary embodiments which are illustrated in the accompanying drawings. In the FIGURES, similar structure will be identified using identical reference characters, as set forth in TABLE 2. It will be understood that the FIGURES are for the purpose of describing particular embodiments and are not intended as limiting. Turning now to FIG. 1, schematic representation of an embodiment of the system for measuring chemical oxygen demand 1 using a higher valence iron species such as Fe(VI) to oxidize organic species. An electrochemical cell that can also transmit light and so operate as a colorimeter is termed a "Spectroelectrochemical cell." Spectroelectrochemical cell 2 comprises an electrolysis tank adapted to perform colorimetric measurements through the anode compartment. For example, on either side of light path 27 are arranged light source and detector components for measuring absorbance of light-absorbing species such as ferrate. Spectroelectrochemical cell 2 includes iron anode 23 and cathode 32, both in electrical communication via circuit 34 with electrochemical workstation 8. Workstation 8 comprises standard electrolytic power supply and monitoring meters, and further houses the spectrometer electronics necessary for the colorimeter. The colorimeter comprises the source module 5 which further includes the light source 14 and a lens 15 for focusing the light along light path 27 to detector module 4. Detector module 4 has conventional components such as a slit, a prism or grating, filter, diode array, and a single channel or multi-channel detector. All of these components are standard components and are well-known to one of ordinary skill. The electrical inputs to the source module 5 and outputs from detector module 4 are from and to, respectively, the electrochemical workstation 8.

Liquid handling system 3 comprises subsystems for reagent delivery, sample introduction and pH optimization. Regent delivery and pH optimization is effected via peristaltic pump 17 that is in fluid communication with acid, base and buffer reservoirs 20, 21 and 22 respectively. Pump 17 delivers reagents to cell 2 via reagent conduit 16 in the general vicinity of anode 23. Sample introduction is via sample inlet 9, sample pump 12 and related fluid conduits and valving. Cathode compartment conduit 35 and associated valving allows admittance of fluid reagents to the cathode compartment (located above separator 28) so that it may be in fluid communication but somewhat compartmentalized from the anode compartment to maximize production of ferrate ion in the anode compartment. Separator 28 may be a sieve or frit or PTFE membrane from Porosex that segregates hydrogen gas within the cathode compartment yet allows current/charge to flow through to the anode compartment.

Other components of the system include the stirrer module 7 and associated stirrer 26 that are located proximate the anode so that ferrate production may be optimized; a vent 31 for venting hydrogen from the cathode compartment; and a temperature optimizing unit 25 for maintaining a given temperature in the cell.

Ferrate produced by this embodiment is represented by the wave 24 which represents ferrate being produced electrochemically in situ. Typical conditions for a steady production of ferrate are discussed in more detail in the Examples which follow. In operation, ferrate ion is produced in the anode compartment by oxidation of the iron anode in the presence of an alkaline hydroxide such as potassium hydroxide to $[FeO_4]^{2-}$ ion. As ferrate is produced on the anode it is mixed into solution, and a first absorbance reading is taken and recorded as the background (also described as the "blank") absorbance. Next, a fixed amount of sample having oxidizable organic chemicals is introduced into the anode compartment, the ferrate is allowed to oxidize any oxidizable organic chemicals present, and after the oxidation is largely complete a second absorbance reading is taken. The color of the ferrate, which is purple-like in high concentration, will fade as it oxidizes the chemical species present and is itself reduced to a lower valence. The difference between the two measurements is calculated in EC workstation 8, and correlated to a lookup table having calibration data and a value for COD is displayed. If operating in batch mode, the EC cell may then be flushed in preparation for the next cycle. Workstation 8 is a typical PC, handheld, smartphone or other computerized device capable of taking incoming digital and analog signals, converting them to data, and calculating and displaying the scientific results.

In the embodiment described above, the overall design of the spectroelectrochemical cell is for batch analysis in that a sampler takes a sample from a sample conduit, then transfers it to the COD measuring system, and an aliquot of sample is admitted to the anode compartment, reagents are added to adjust pH and, and the sample chemicals are oxidized all while the anode compartment is closed to further sample introduction. This allows for more sensitive detection, but also suffers from the usual handicap of a batched sampling environment. This embodiment may be modified to be a flow-through design where sample continuously flows through the anode compartment and results are continuously available in real time. In order to determine the quantity of COD in the sample as it flows through, the calibration table data will have to reflect the dynamic environment of the spectrophotochemical cell. This real-time process embodiment is described in more detail in the following embodiment.

Detection of the change in ferrate concentration may also be achieved by electrochemical means if a voltage detecting system is used to measure the potential generated in the anode portion of the cell. Assuming the potential reading is not significantly complicated by other species present, the potential provides a means to determine the concentration of ferrate present in real time.

In one embodiment, a modification of the above process apparatus separates the spectrophotometric cell from the electrolyzer cell, thereby separating the production of the ferrate from its consumption in the presence of COD-containing liquid sample. FIGS. 2A and 2B disclose a schematic representation of the apparatus of this embodiment, FIG. 2A is the side view and FIG. 2B is the top-down view. Hydroxide solution 1 is pumped or drawn into electrochemical cell ("EC") 7, which is of standard design and has an iron anode 4 and a cathode 5. Both electrodes are in electrical communication with a power supply (not shown) for energizing the solution. Cathode 5 has a hydrogen-restrictive membrane 6 around it so that hydrogen does not flow back into solution. Ferrate 8 is produced in solution in the EC cell 7 and is in solution at a high pH engendered by the hydroxide solution 1. Exit stream 2 connects the output of the EC cell to a pair of light source/detector combinations 9/10 and 11/12, respectively. Each pair comprises a colorimetric light path for measuring the absorbance of ferrate ion across the exit stream. Not shown are transparent conduits or transparent windows in conduits for the passage of the light sources. The arrow labeled 3 represents a sample stream being admitted to and mixed with the exit stream 2 at the intersection of the head of the arrow 3 and the line representing the exit stream 2. Since the sample is admitted and mixed at a point downstream of the first light source/detector combination, the source/detector combination 9/10 measures the background absorbance reading while source/detector combination 11/12 measures the sample absorbance reading. As described above, their difference is correlated to a certain amount of COD in the sample via a calibration table.

The method of the above-described apparatus is directed to a method for measuring chemical oxygen demand comprising providing a light-transparent sample cell in liquid communication with the EC cell; providing a light-transparent blank cell in liquid communication with the EC cell; providing an amount of alkaline hydroxide to said liquid cell contents; applying a current density to the EC cell at a sufficient electric potential to oxidize a portion of the iron anode to create a solution comprising Fe(VI); providing one or more light sources for projecting light through either or both blank and sample cells; providing one or more detectors for detecting the light passing through either or both blank and sample cells; optimizing pH of the Fe(VI) solution prior to introduction of the liquid cell contents into the sample cell to between about 3 and about 11; combining the sample and the Fe(VI) solution in the sample cell; and measuring and comparing the light absorbance in both blank and the sample cells at a wavelength diagnostic of depletion of ferrate ion, thereby determining the chemical oxygen demand of the sample.

Another embodiment of the apparatus is illustrated by FIGS. 3A and 3B. The difference between this embodiment and the previous embodiment is apparent in that exit stream 2 splits into a blank stream 3 and a first sample stream 4. Each stream 3, 4 has a light source/detector combination 11/12 and 13/14 for the blank and first sample streams, respectively. Light source/detector combination 11/12 is dedicated to the blank reading and so measures the background signal of the exit stream prior to introduction of sample. Arrow 5 represents the point at which the sample is introduced.

Figure 7:
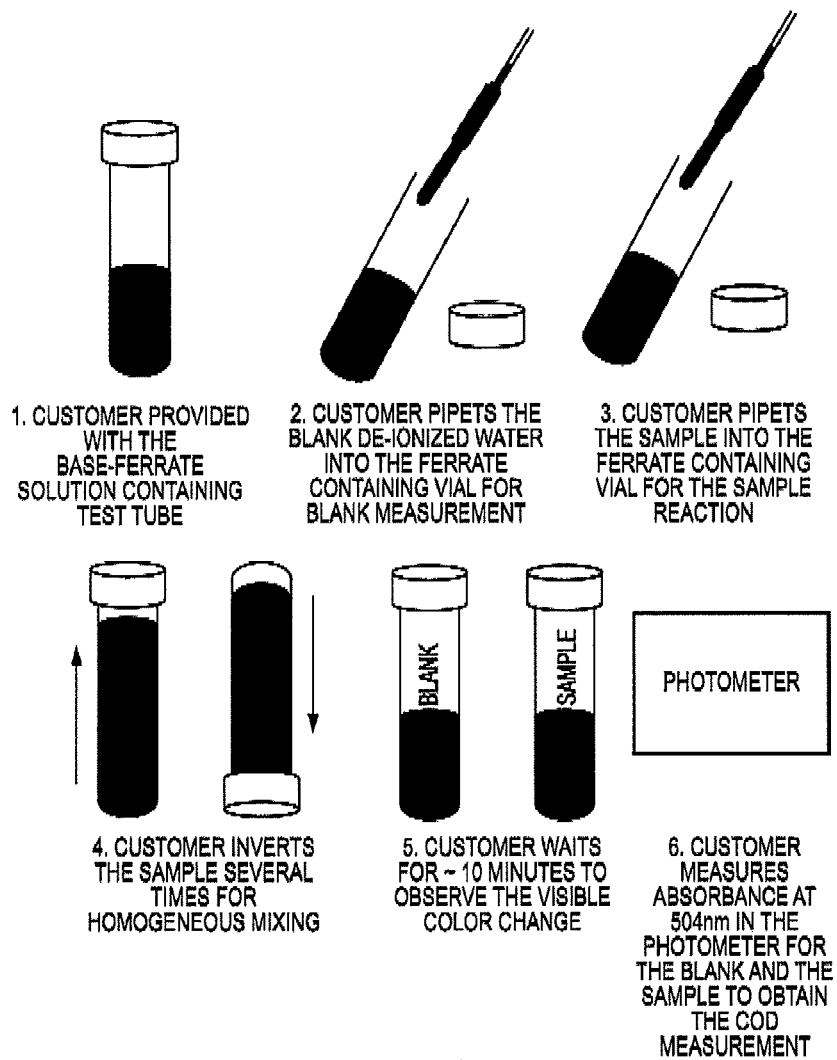
FIG. 7 shows a pictogram of a standard use model for dichromate lab use.

Another embodiment uses separate blank and sample cuvettes. FIG. 7 illustrates the present method for measuring chemical oxygen demand in a laboratory environment using at least one higher valence iron species, including providing a known amount of Fe(VI) into a first container. An appropriate source of Fe(VI) may be $K_2FeO_4$, as previously mentioned. Typically, an amount sufficient to oxidize any foreseeable amount of organic matter is introduced. A water sample suspected of containing materials having oxygen demand is introduced into the same first container. The pH is then optimized for the particular chemical species known to be present in the sample. The pH range is initially broad (between 3 and 11), but is ascertainable by a process of pH optimization, discussed above. This optimized pH will then begin the oxidation by ferrate of the oxidizable species present. A blank is generated to be used as a baseline measurement. A known amount of Fe(VI) is introduced into a second container, and then a blank water sample is added to the second container. pH of the blank in the second container is adjusted to be substantially the same as the sample. The COD of the sample is quantified by measuring a parameter indicative of the difference in concentration of the higher valence iron species (optical absorbance or electrical potential) between the water sample and the blank water sample caused by the materials having oxygen demand whereby said oxygen demand is quantified. Quantification is attained by subtracting the sample absorbance value from the baseline absorbance and then correlating the net absorbance with a calibrated value. To improve the accuracy of the quantified oxygen demand it is desirable to measure the oxygen content before, after and during the reaction of ferrate with organics in the aqueous sample. Some of the side reactions during the COD measurement produce oxygen due to oxidation of water or from decomposition of $FeO_4^{2-}$. Measuring oxygen before, after and during the COD analyses provides a means to compensate for the false positives due to the side reactions that can occur during the COD quantification process.

The use of ferrate as an oxidant effective for COD analyses has not previously been recognized. Carr et al. attempted with no success to improve the dichromate COD method by the use of ferrate ion as an alternate or primary oxidant. Carr, J., USE OF POTASSIUM FERRATE IN OXYGEN DEMAND MEASUREMENT. U.S. Environmental Protection Agency, Washington, D.C., EPA/600/7-77/099 (NTIS PB271439), 1977. Work has been done using ferrate as a general purpose oxidant to treat waste water.

The methods for measuring chemical oxygen demand disclosed herein determine both carbonaceous chemical oxygen demand (CCOD) and nitrogenous chemical oxygen demand (NCOD) of a sample. In order to obtain chemical oxygen demand comparable to that obtained in the dichromate method (i.e., CCOD), it is necessary to prevent nitrogen-containing compounds from contributing to the oxidation in a sample by ferrate ion. One way to do so is to add a nitrogen inhibitor. In other words, in order to obtain CCOD by itself, a nitrogen inhibitor (e.g., Hach® nitrification inhibitor for BOD, Formula 2533™, TCMP) may be added to a sample. The nitrogen inhibitor inhibits oxidation of nitrogen-containing compounds and permits oxidation of carbon-containing compounds. COD is determined without use of the nitrogen inhibitor. Also, upon determining CCOD and COD, NCOD may be determined by subtracting CCOD from COD as COD=CCOD+NCOD. The ferrate COD method is similar to the BOD5 method which has the similar equation BOD=CBOD+NBOD. This enables the ferrate COD method to correlate to BOD5 method more effectively than the dichromate COD method.

Accordingly, also disclosed herein is a method for determining carbonaceous chemical oxygen demand in a sample, comprising: preventing nitrogen-containing compounds from contributing to oxidation in the sample by ferrate ion; after the preventing operation, adding ferrate ion to the sample; measuring a parameter indicative of the amount of ferrate ion in the sample; and determining a carbonaceous chemical oxygen demand value of the sample based on the measured parameter. In one embodiment, the preventing operation comprises adding a nitrogen inhibitor to the sample. In another embodiment, the method further comprises: adding ferrate ion to a blank sample; and measuring a parameter indicative of the amount of ferrate ion in the blank sample, and the determining operation comprises calculating a difference in the measured parameters between the sample and the blank sample and determining the carbonaceous chemical oxygen demand value of the sample based on the difference. In yet another embodiment, the measuring operation regarding the sample comprises passing light through the sample and measuring an absorbance of light passed through the sample at a wavelength diagnostic of ferrate ion; and the measuring operation regarding the blank sample comprises passing light through the blank sample and measuring an absorbance of light passed through the blank sample at the wavelength diagnostic of ferrate ion.

The methods for measuring chemical oxygen demand disclosed herein may be used to determine assimilable organic carbon (AOC) of a sample. AOC is the amount of carbonaceous materials that is assimilated by bacteria and characterizes the health and growth potential of bacteria. In reverse osmosis processes, bacteria growth leads to biofouling on membrane components, which in turn causes additional hydraulic resistance and decreases efficiency. See Quek et al., Bio-Electrochemical Sensor for Fast Analysis of Assimilable Organic Carbon in Seawater, J Biosens Bioelectron 2014, 5:2. Accordingly, AOC can measure the effectiveness of reverse osmosis, the potential for biofouling, and the need for preventative measures to avoid biofouling. Prophetic Example 3 herein explains how the methods disclosed herein may be utilized for determining AOC.

The methods for measuring chemical oxygen demand disclosed herein may be used to determine the COD of seawater. Example 4 herein illustrates how the methods disclosed herein may be utilized for determining COD of seawater.

EXAMPLES

Example 1

Electrochemical Production of Potassium Ferrate:
Potassium ferrate ($K_2Fe_2O_4$) was made according to the synthesis described by Diwakar Tiwar et al., www.lntechopen.com, "Ferrate (VI) in the Treatment of Wastewater: a New Generation Green Chemical," with the following differences. 1) the anodic and cathodic compartments are separated by a frit or membrane as previously described; 2) maintenance of a constant temperature using a water bath for the EC cell at 60 C; 3) use of 14.5 M KOH; and 4) use of steel wool or CRS 1018 for electrodes. In general, an electrochemical cell operated at about 300-500 ml capacity was equipped with two CRS 1018 (cold rolled steel, 0.15-0.2% carbon, 0.6-0.9% Mn, 0.04% P, 0.05% S) flat iron electrodes, dimensions 6.5 cm×2.5 cm×0.5 cm. The cathode was segregated from the rest of the EC cell by an open-topped glass tube having a porous PTFE frit, 1/16" pore size, positioned across the bottom so that evolved Hydrogen gas could not readily dissolve into the hydroxide bath. A hot water bath surrounded the EC and was maintained at 70 C although the working range is from 35 C to 80 C. A DC power supply (Shenzen Mastech DC power supply) or an electrochemical work station (CHI Instrument, Model 760C) can be used to energize the cell. Typical current density required is 5 mA/$cm^2$ for approximately 6 hours will generate sufficient ferrate. The cell including the cathodic compartment was filled with 14.5M KOH. The pH of the solution in the cell is 14. NaOH may also be used either in combination or alone.

Example 2

Figure 4A:
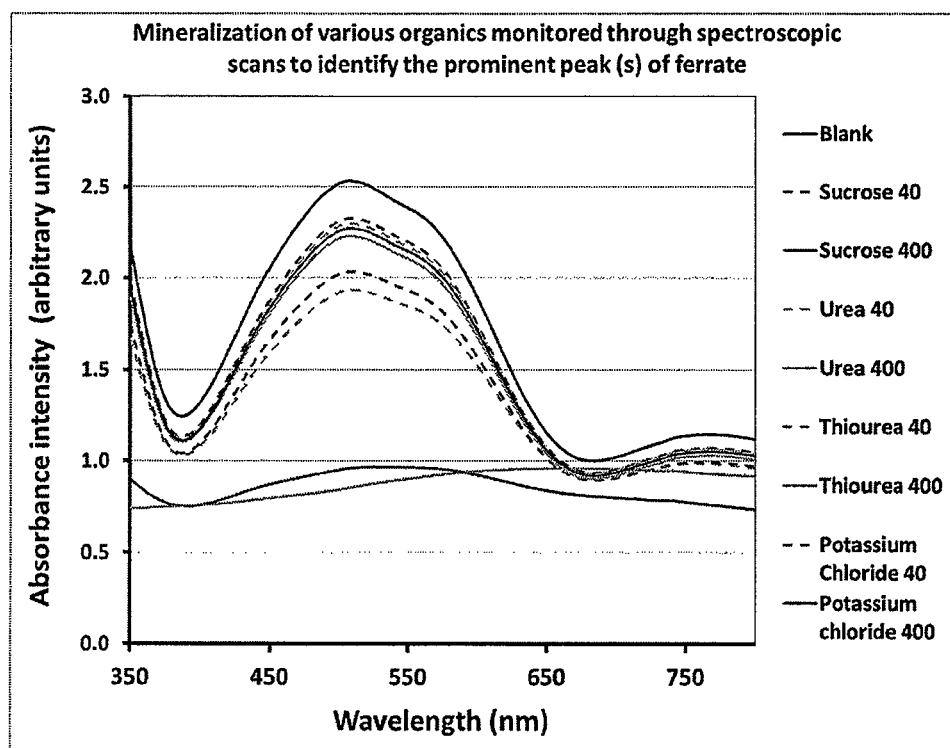
FIG. 4A is a series of spectroscopic scans acquired at ~10 min. after the addition of the electro-synthesized liquid ferrate (oxidant) to the sample/blank solution.
Figure 4B:
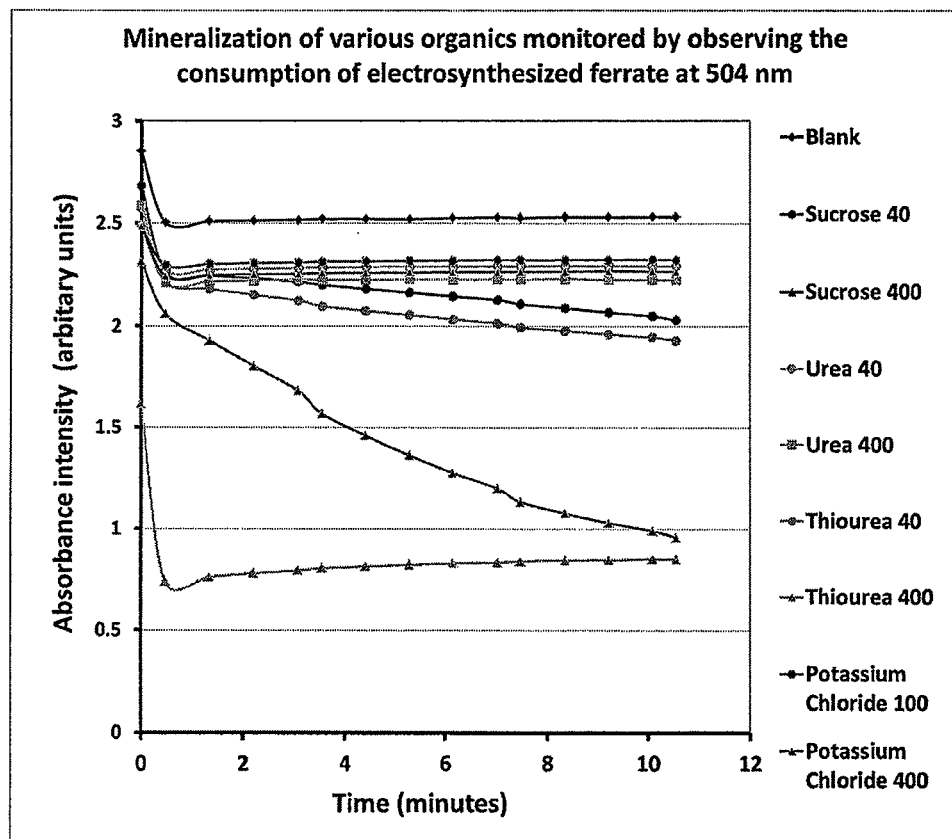
FIG. 4B is a series of photometric measurements taken at 500-515 nm between the blank (straight ferrate solution containing no chemical oxygen demand, e.g. D1 water) and the sample solutions containing ferrate, which provide the basis for quantification of the chemical oxygen demand of the sample.

Oxidation of Organic Compounds in a Laboratory Model:
Standard COD apparatus was used to oxidize different concentrations of Sucrose, Urea, Thiourea and Potassium Chloride at 40 mg/L and 400 mg/L, and then measure the degradation in spectroscopic absorbance of ferrate ion at 504 nm. To a 35 ml glass cuvette, 8 cm×2 cm, with a twist-top closure was added 6 ml of deionized water, 5 ml of 5 mM potassium ferrate solution, and 3 ml sample or blank. Total volume in the spectroscopic cuvette was 14 ml. The solutions were allowed to oxidize for approximately ten minutes, then measured for absorbance. These steps are described in the schematic of FIG. 7. A Hach brand DR6000 spectrophotometer was used to measure absorbance of the blank and samples at 504 nm. Results are shown in FIGS. 4A and 4B. FIG. 4A is a series of spectroscopic scans acquired at ~10 minutes after the addition of the electro-synthesized liquid ferrate (oxidant) to the sample/blank solution. FIG. 4B is a series of differential photometric measurements taken at 504 nm between the blank (ferrate) and the sample solutions containing ferrate, which provide the basis for quantification of the chemical oxygen demand of the sample.

Sucrose and thiourea were oxidized within 10 min. without digestion. Urea had almost the same recovery rates as the dichromate method. Unlike other methods, ferrate did not oxidize chloride and thus this method was not affected by the common interferant molecule (chloride) encountered in other COD measurements. Because the redox potential of Sucrose is much lower than ferrate it gets oxidized within 10 min., unlike the Dichromate oxidation which needs digestion because of the proximity of formal potentials between Dichromate and Sucrose. Possible reasons for the ferrate not oxidizing chloride are the elimination of the digestion step, the adoption of higher pH conditions, the anionic characteristics of ferrate and/or different coordination characteristics of ferrate over other oxidants. The other possible reasons include slower kinetics, and higher preference for organics by ferrate. This is a distinct advantage over the prior art method.

Figure 5:
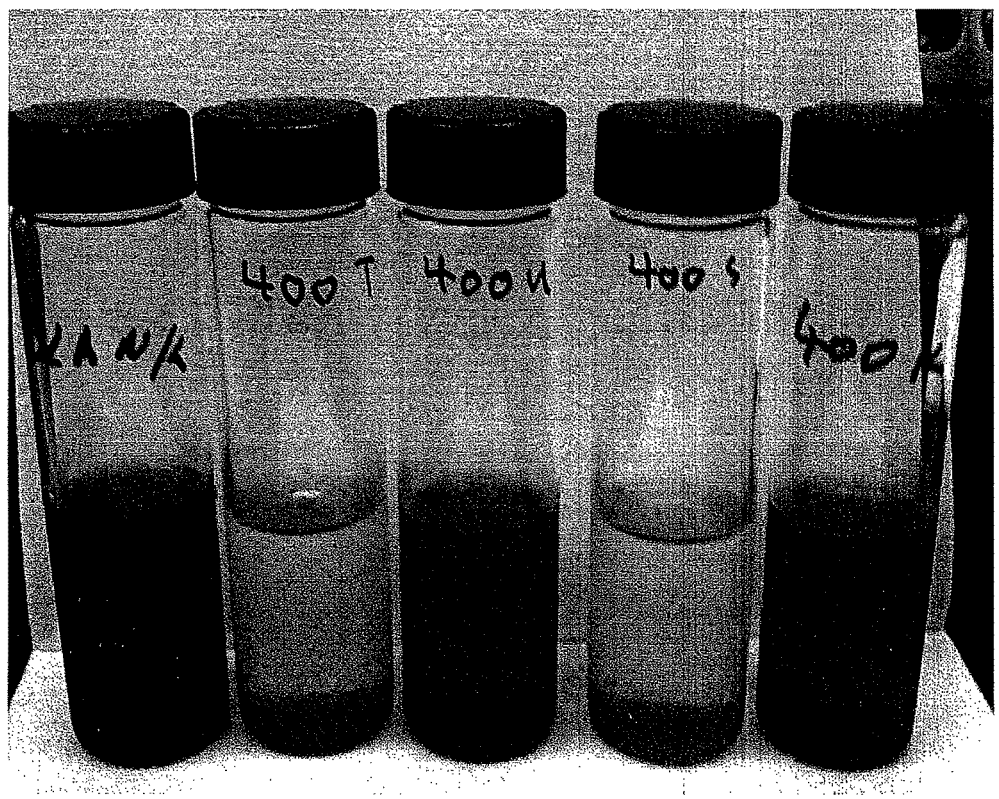
FIG. 5 shows labelled reagent cuvettes, where visible color change indicates the oxidation reaction of ferrate with model compounds including (from left to right): Blank, Thiourea, Urea, Sucrose and Potassium Chloride (an interferant).

FIG. 5 shows the labelled reagent cuvettes. Visible color change indicating the oxidation reaction of ferrate with model compounds including (from left to right): Blank, Thiourea, Urea, Sucrose and Potassium Chloride.

Figure 9:
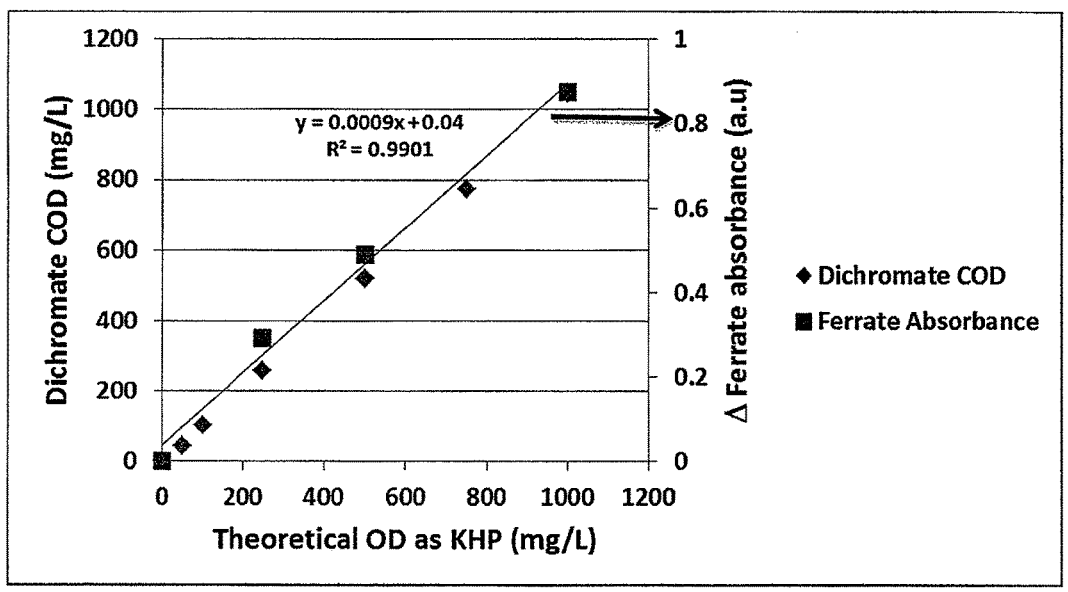
FIG. 9 is a comparison of the oxidation efficiencies of dichromate versus ferrate, where oxidation of KHP using both separately is plotted against amount of COD using KHP as the proxy.

FIG. 9 shows a comparison of dichromate and ferrate oxidation of potassium hydrogen phthalate (KHP), the generally-accepted standard for COD. There is close correlation of results.

Prophetic Example 3

Determination of AOC:

The following materials would be needed to determine AOC of a sample: standard bacterial microorganisms (e.g. *Pseudomonas fluoresens* and *Spirillum*); an incubator; organic free water; ferrate; and a food source for the microorganisms including monosaccharides, primary amines, and low molecular weight (<10,000 nominal molecular weight) dissolved organic carbon.

An amount of the food source is added to the microorganisms and the initial amount of organic compounds in the food source is determined by ferrate oxidation. The decrease in the ferrate absorbance due to the oxidation of the organic compounds is used to quantify the initial amount of organic compounds. This initial amount of organic compounds is represented by the value X.

The test waters containing the microorganisms are then incubated at 15° C. and sampled repeatedly to establish stable values that indicate the completion of the growth of the microorganisms. After completion, the microorganisms are filtered and the final amount of organic compounds in the food source is determined by ferrate oxidation. The decrease in the ferrate absorbance due to oxidation of the organic compounds is used to quantify the remaining amount of organic compounds. This remaining amount of organic compounds is represented by the value Y.

The difference between X and Y is the AOC.

Alternatively, the microorganisms themselves are oxidized by ferrate before incubation and then after incubation. The decrease in ferrate absorbance due to oxidation of the microorganisms provides the AOC.

AOC is typically a small amount. Accordingly, the decrease in ferrate absorbance due to oxidation is typically small and an alternative indicator such as 2,2'-azino-bis(3-ethylbenzothiazoline-6-sulfonate) (ABTS) can be used. ABTS reacts with ferrate in a stoichiometry of 1:1 in excess of ABTS. ABTS forms a green radical cation (ABTS.+) that can be measured spectrophotometrically at 415 nm.

Example 4

Determination of COD of Seawater:

Ferrate absorbance at 680, 790 or 510 nm was measured in seawater spiked with KHP and glucose separately. Solutions of KHP and glucose were prepared in seawater at five concentrations each (35, 50, 100, 200, and 300 mg/L $O_2$). The oxidation reagent consisted of ~55 mM ferrate (~18% active ingredient) and 0.2 M potassium phosphate diabasic buffer. For each sample vial, the formulary was about 56× so that 0.125 mL of sample was added to 6.85 mL of ferrate oxidation reagent for a total volume of 6.975 mL. The vials were inverted four times and placed in the centrifuge at 3000 rpm for two minutes. The samples were then heated in the digester blocks at 80° C. for 20 minutes. Immediately after digestion, the timer was set for 30 minutes and the vials were inverted four times and centrifuged again. At the end of the 30 minute cooling period, the vials were centrifuged for a third time and then final absorbance measurements were recorded at appropriate wavelength.

Figure 10:
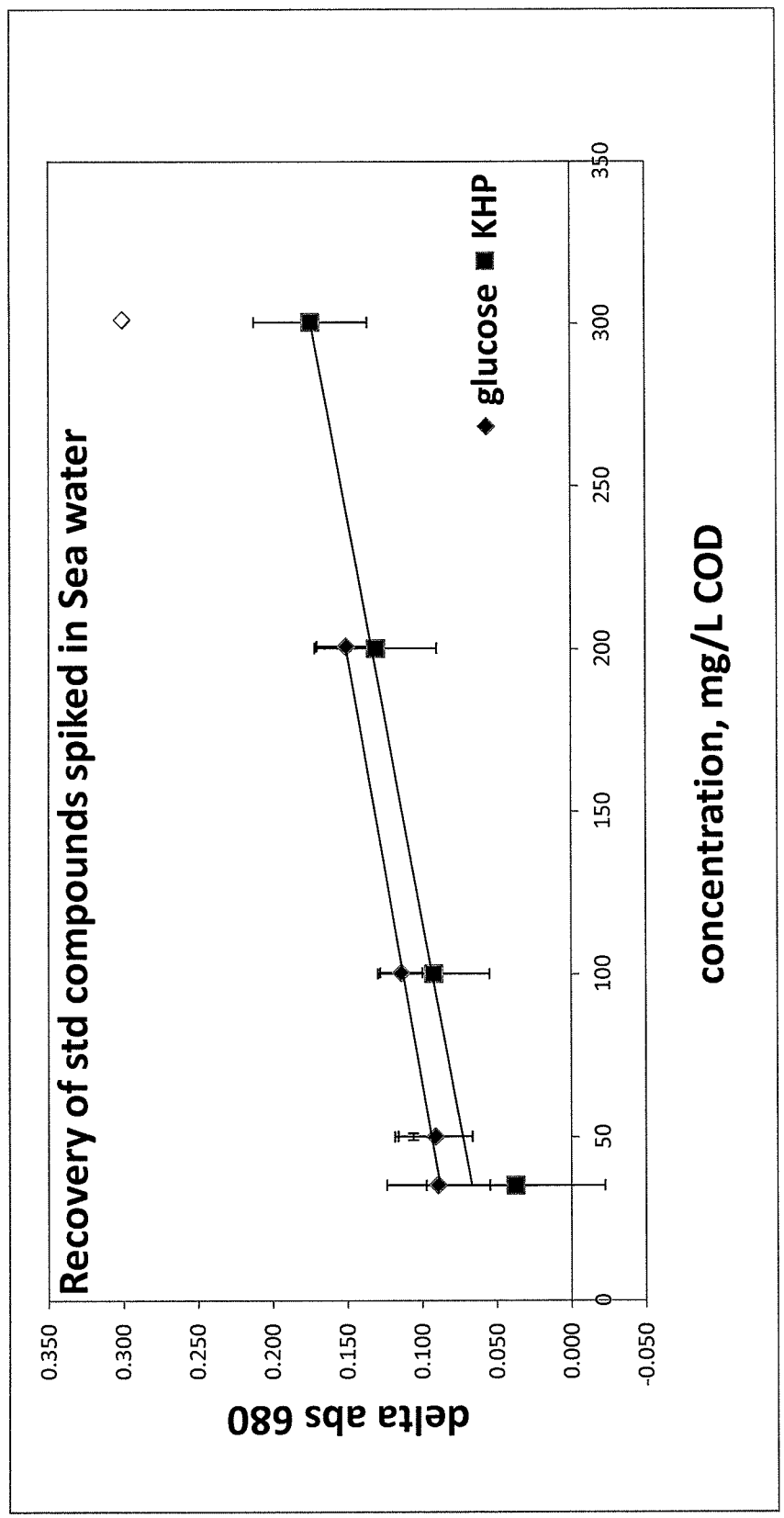
FIG. 10 is a graph of oxygen concentration in seawater versus the change in ferrate absorbance at 680 nm.

FIG. 10 shows the recovery of KHP and glucose at different concentrations. The change in absorbance at 680 nm was determined by calculating the difference between the absorbance of a blank and a sample at 680 nm. As the concentration of the organics increased, there was an increase in the change in absorbance. The linear trend for both KHP and glucose showed that ferrate proportionally oxidizes these organic compounds as the concentration of these organic compounds increases. This demonstrated that oxidation of KHP and glucose can be achieved in seawater using ferrate as the oxidant in the investigated concentration range.

TABLE 2

Components Of Apparatus

| No. | Description |
|---|---|
| 1 | System for measuring COD using ferrate |
| 2 | Spectroelectrochemical cell |
| 3 | Reagent delivery system; pH optimizing unit |
| 4 | Detector module for photometer |
| 5 | Source module for the photometer |
| 6 | Cathode compartment conduit |
| 7 | Stirrer module |
| 8 | Electrochemical workstation |
| 9 | Sample inlet |
| 10 | Pressure gauge |
| 11 | Valve |
| 12 | Sample Pump |
| 13 | Pressure optimizing device |
| 14 | Light source |
| 15 | Lens |
| 16 | Reagent conduit |
| 17 | Peristaltic pump module for reagent/fluid delivery |
| 18 | "Lobe" of the peristaltic pump in the "OFF" position for positive displacement of the fluid |
| 19 | "Lobe" of the peristaltic pump in the "ON" position for positive displacement of the fluid |
| 20 | Acid reagent |
| 21 | Base reagent |
| 22 | Buffered reagent |
| 23 | Iron anode |

TABLE 2-continued

Components Of Apparatus

| No. | Description |
|---|---|
| 24 | Ferrate produce electrochemically |
| 25 | Temperature optimizing unit |
| 26 | Stirrer for optimizing the yield of ferrate |
| 27 | Light path for detecting the ferrate depletion |
| 28 | Separator to separate anode and cathode for increasing the efficiency of ferrate production |
| 29 | Outlet for further analyses of the sample, ferrate or reagents |
| 30 | Hydrogen bubbles produced at the cathode |
| 31 | Vent to degas the bubbles |
| 32 | Cathode |
| 33 | Circuit for measuring the voltage developed across the anode and cathode |
| 34 | Circuit for applying the required current to produce ferrate |
| 35 | Conduit to allow liquid communication to the cathodic chamber |

The foregoing has been presented for purposes of illustration and description and is not intended to be exhaustive or limiting. Many modifications and variations are possible in light of the above teaching.

The invention claimed is:

1. A method for measuring chemical oxygen demand in a flow-through EC cell having an integrated spectrophotometer, comprising:
   providing the flow-through EC cell adapted to electrolyze liquid cell contents, wherein the flow-through EC cell comprises an iron anode, a cathode and a light-transparent sample cell;
   providing an amount of alkaline hydroxide to the liquid cell contents;
   generating optically active reagents in-situ by applying a current density to the liquid cell contents at an electrical potential sufficient to oxidize a portion of the iron anode to a higher valence comprising Fe(VI);
   detecting a concentration of the generated Fe(VI) by measuring, using an electrochemical measurement, a potential generated across the iron anode;
   providing a light source for projecting light through the sample cell;
   providing a detector for detecting the light after passing through the sample cell;
   optimizing pH of the liquid cell contents to between about 3 and about 11 such that oxidizable organic species are detectable;
   measuring the baseline light absorbance at a wavelength diagnostic of ferrate ion;
   introducing a sample into the EC cell in proximity to the anode, wherein the Fe(VI) oxidizes organics of the sample causing a decrease of ferrate ion;
   measuring the light absorbance of the sample at a wavelength diagnostic of depletion of ferrate ion; and
   determining the chemical oxygen demand of the sample by comparing the light absorbances.

2. The method of claim 1, wherein the cathode comprises iron.

3. The method of claim 1, wherein the alkaline hydroxide is chosen from alkali metal hydroxides.

4. The method of claim 1, wherein the temperature of the EC cell is maintained between about 35 C and about 75 C.

5. The method of claim 1, wherein the current density ranges from about 0.001 A/cm$^2$ to about 10 A/cm$^2$.

6. The method of claim 1, additionally comprising the step of:
   monitoring voltage in the EC cell as the liquid cell contents are introduced as an indication of oxygen demand.

7. The method of claim 1, wherein the Fe(VI) comprises $[FeO_4]^{2-}$.

8. The method of claim 1, wherein optimizing pH comprises the additional steps of:
   changing the pH of an aliquot of a first sample to a first pH and measuring its absorbance;
   changing the pH of a second aliquot of the same sample to a second pH and measuring its absorbance;
   determining the difference between the first and second absorbance measurements, whereby the difference indicates the oxidation rate of the organic compounds at the selected pHs; and
   repeating the first three steps to find the maximum difference thereby identifying the optimal pH for the sample.

* * * * *